United States Patent
Sawanobori

(10) Patent No.: US 10,390,778 B2
(45) Date of Patent: Aug. 27, 2019

(54) GANTRY

(71) Applicant: Toshiba Medical Systems Corporation, Otawara-shi (JP)

(72) Inventor: Tadashi Sawanobori, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 349 days.

(21) Appl. No.: 15/295,543

(22) Filed: Oct. 17, 2016

(65) Prior Publication Data

US 2017/0105692 A1  Apr. 20, 2017

(30) Foreign Application Priority Data

Oct. 19, 2015  (JP) .................................. 2015-205577
Sep. 9, 2016  (JP) .................................. 2016-177081

(51) Int. Cl.
A61B 6/00 (2006.01)
A61B 6/03 (2006.01)

(52) U.S. Cl.
CPC ............ A61B 6/4488 (2013.01); A61B 6/035 (2013.01)

(58) Field of Classification Search
None
See application file for complete search history.

(56) References Cited

U.S. PATENT DOCUMENTS

| 6,909,775 B2 | 6/2005 | Ray et al. |
| 8,282,278 B2 | 10/2012 | Sharpless |
| 2007/0274437 A1* | 11/2007 | Schindler ............... A61B 6/035 378/20 |
| 2009/0279660 A1* | 11/2009 | Takamatsu ............ A61B 6/035 378/19 |
| 2014/0169531 A1 | 6/2014 | Kodaira |
| 2016/0235378 A1* | 8/2016 | Yun ...................... A61B 6/4488 |

FOREIGN PATENT DOCUMENTS

| JP | 9-276262 | 10/1997 |
| JP | 2004-121717 | 4/2004 |
| JP | 2004-195224 | 7/2004 |
| JP | 2010-227382 | 10/2010 |
| JP | 2011-505187 | 2/2011 |
| JP | 2011-143063 | 7/2011 |
| JP | 5159965 | 3/2013 |

* cited by examiner

Primary Examiner — Hoon K Song
(74) Attorney, Agent, or Firm — Oblon, McClelland, Maier & Neustadt, L.L.P.

(57) ABSTRACT

A gantry according to an embodiment includes a rotating frame, a fixing mechanism, and an air sending mechanism. The rotating frame includes an X-ray tube and an X-ray detector configured to detect X-rays emitted from the X-ray tube. The fixing mechanism is configured to support the rotating frame so as to be rotatable on a rotation axis. The air sending mechanism is installed on a lateral face on the outer circumferential side of the rotating frame with respect to the rotation axis and is configured to send air sucked in from the exterior of the rotating frame to the rotation axis side of the rotating frame. The air sending mechanism is installed so as to be offset from the rotating frame.

13 Claims, 10 Drawing Sheets

GANTRY

CROSS-REFERENCE TO RELATED APPLICATIONS

This application is based upon and claims the benefit of priority from Japanese Patent Application No. 2015-205577, filed on Oct. 19, 2015, and Japanese Patent Application No. 2016-177081, filed on Sep. 9, 2016; the entire contents of which are incorporated herein by reference.

FIELD

Embodiments described herein relate generally to a pantry.

BACKGROUND

Conventionally, an X-ray Computed Tomography (CT) apparatus is configured to cool the heat within the gantry thereof by, for example, arranging air sucked in from a lower part of the front face of the gantry to flow to the ceiling face of the gantry by using a fan installed in an upper part of the gantry and further discharging air from the ceiling face of the gantry to the exterior of the gantry.

DETAILED DESCRIPTION

Exemplary embodiments of a gantry will be explained, with reference to the accompanying drawings. The gantry according to the exemplary embodiments is a gantry included in an X-ray Computed Tomography (CT) apparatus. Possible embodiments are not limited to the embodiments described below. Further, in principle, the description of each of the embodiments is applicable to any other embodiments.

A gantry according to an embodiment includes a rotating frame, a fixing mechanism, and an air sending mechanism. The rotating frame includes an X-ray tube and an X-ray detector configured to detect X-rays emitted from the X-ray tube. The fixing mechanism is configured to support the rotating frame so as to be rotatable on a rotation axis. The air sending mechanism is installed on a lateral face on the outer circumferential side of the rotating frame with respect to the rotation axis and is configured to send air sucked in from the exterior of the rotating frame to the rotation axis side of the rotating frame. The air sending mechanism is installed so as to be offset from the rotating frame.

First Embodiment

Figure 1:
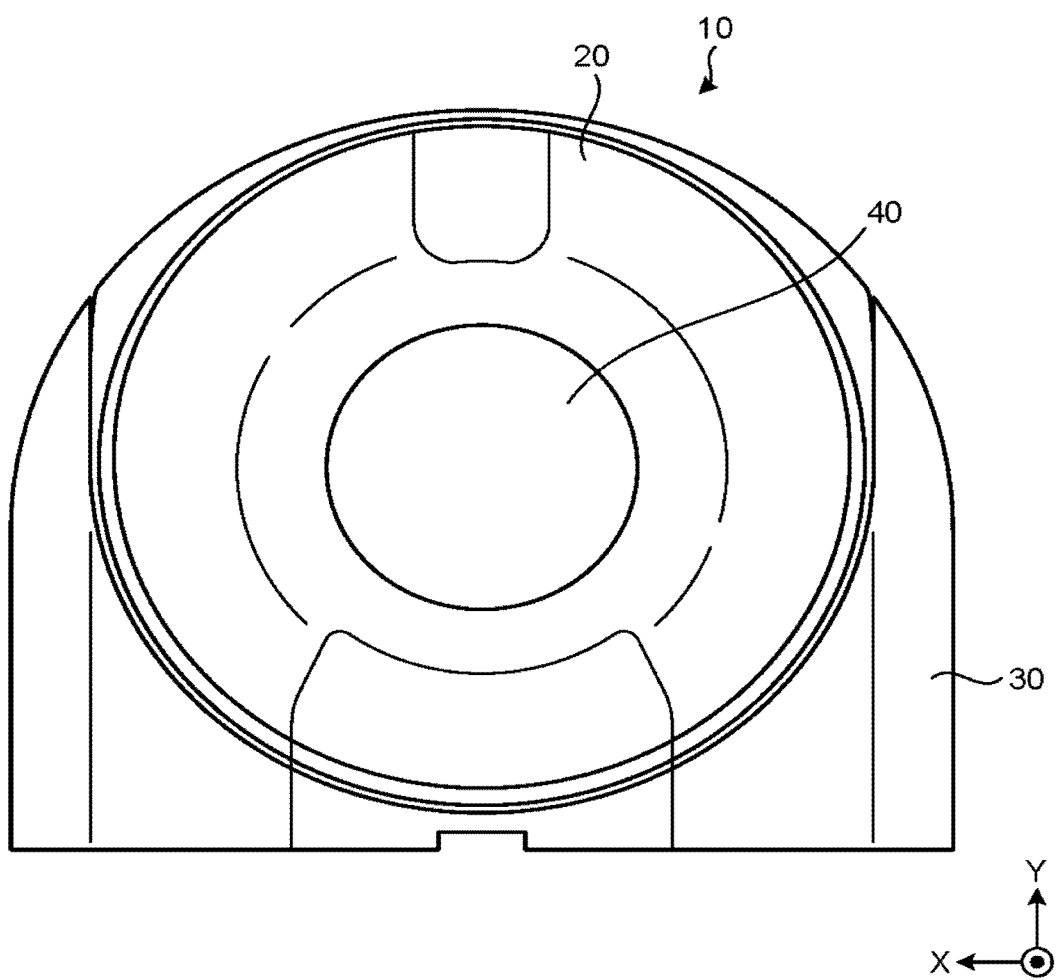
FIG. 1 is a front view illustrating a gantry according to a first embodiment.
Figure 2:
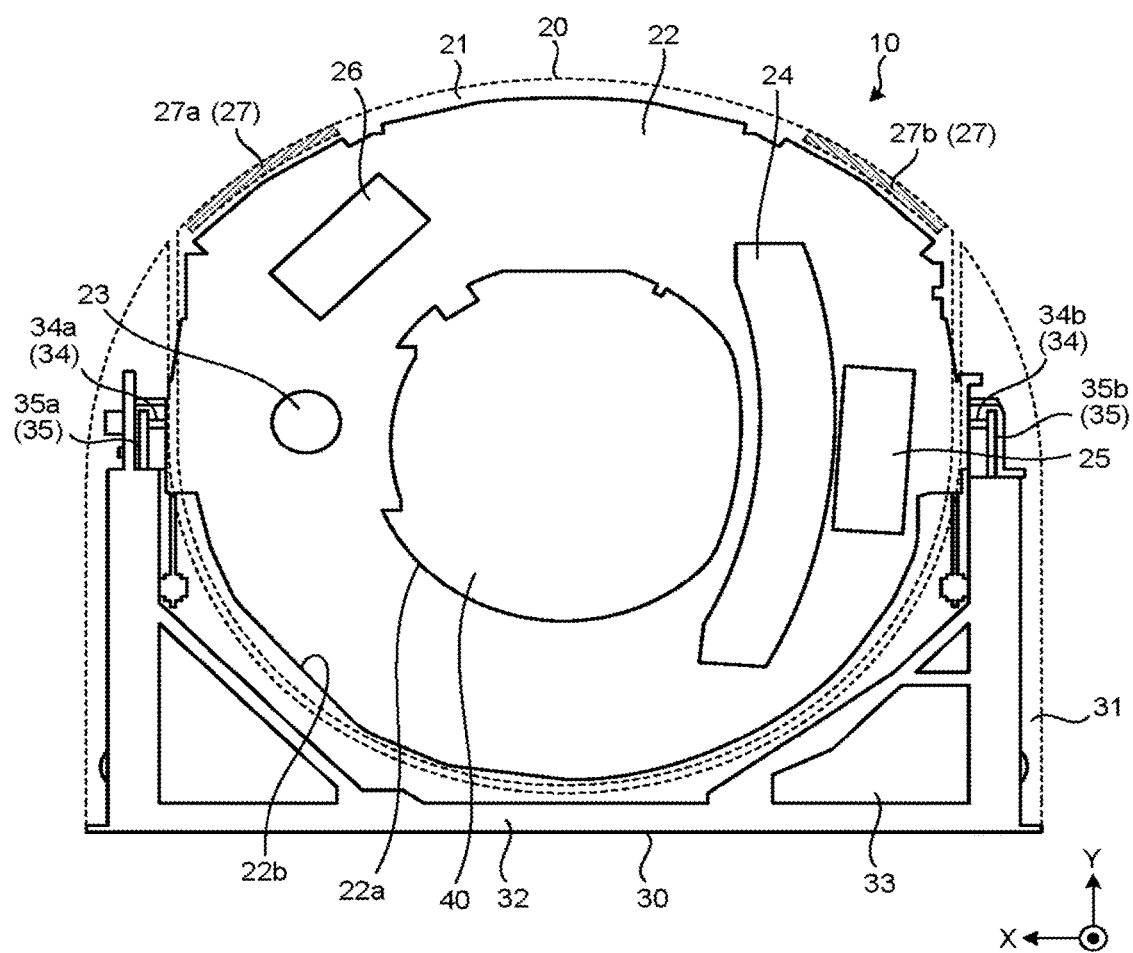
FIG. 2 another front view illustrating the gantry according to the first embodiment.

FIGS. 1 and 2 are front views of a gantry 10 according to a first embodiment. FIG. 1 illustrates the gantry 10 to which a cover is attached, whereas FIG. 2 illustrates the gantry 10 to which the cover is not attached.

As illustrated in FIG. 1, the gantry 10 includes a rotating mechanism 20 and a fixing mechanism 30. Further, the gantry 10 is provided with an opening 40 into which an examined subject (hereinafter, "patient") is inserted. Further, as illustrated in FIG. 1, a Cartesian coordinate system having X-, Y-, and Z-axes is defined with the gantry 10. In other words, the X-axis indicates the horizontal direction, while the Y-axis indicates the vertical direction, and the Z-axis indicates the direction along the central axis of the opening 40. In the Cartesian coordinate system, the directions indicated by the arrows are the positive directions.

As illustrated in FIG. 2, the rotating mechanism 20 includes a cover 21 and a rotating frame 22. The cover 21 is configured to cover the rotating frame 22 and to protect the rotating frame 22. On the over 21, exhaust fans 27a and 27b (explained later) are installed. In FIG. 2, the cover 21 is indicated with a broken line.

As illustrated in FIG. 2, the rotating frame 22 is an annular-shaped frame formed with an annular region 22a that forms the opening 40 and an annular region 22b that surrounds the annular region 22a. For example, the rotating frame 22 includes, as constituent elements thereof, an X-ray tube 23, an X-ray detector 24, a Data Acquisition System (DAS) 25, and an oil cooler 26. Also, the rotating frame 22 may include other constituent elements such as electrical component parts.

In the present example, the constituent elements included in the rotating frame 22 are either directly or indirectly attached to the inside of the annular region 22b of the rotating frame 22. In other words, the constituent elements are attached to the side on which centrifugal forces act, while the rotating frame 22 is rotating. As a result, even when the rotating frame 22 is rotating, the constituent elements are stably fixed to the rotating frame 22. In the following sections, the vicinity of the annular region 22b will be referred to as an outer circumferential side of the rotating frame 22, whereas the vicinity of the annular region 22a will be referred to as an inner circumferential side of the rotating frame 22. More specifically, the inner circumferential side of the rotating frame refers to such a region of the rotating frame 22 that is positioned between the constituent elements that are either directly or indirectly attached to the inside of the annular region 22b and the annular region 22a.

Further, for example, the rotating frame 22 supports the X-ray tube 23 configured to emit X-rays and the X-ray detector 24 configured to detect the X-rays emitted from the X-ray tube 23 so as to be rotatable around the patient. In other words, the rotating frame 22 supports the X-ray tube 23 and the X-ray detector 24 so as to oppose each other while the patient is interposed therebetween and is rotated by a driving mechanism 33 (explained later) at a high speed on a circular orbit centered on a rotation axis. In this situation, for example, the patient is inserted into the opening 40 so as to be placed at the center of the rotation axis. In the present example, the rotation axis of the rotating frame 22 is set in the Z-axis direction that substantially passes the center of the opening 40.

The DAS 25 is configured to acquire projection data from X-ray detection data detected by the X-ray detector 24. Further, the DAS 25 outputs the acquired data to a console (oft illustrated). Accordingly, the console reconstructs CT image data from the acquired projection data.

The fixing mechanism 30 includes a cover 31 and a fixing frame 32. The cover 31 is configured to protect the fixing frame 32. In FIG. 2, the cover 31 is indicated with broken lines. The fixing frame 32 includes the driving mechanism 33 and supports the rotating frame 22 as to be rotatable on the rotation axis thereof. In other words, the driving mechanism 33 causes the X-ray tube 23 and the X-ray detector 24 to revolve on a circular orbit centered on the patient, by driving the rotating frame 22 to rotate. Further, the fixing mechanism 30 includes tilting shafts 34a and 34b and bearings 35a and 35b. The fixing mechanism 30 is capable of supporting the rotating frame 22 so as to be tilted at a predetermined angle with respect to the tilting shafts 34a and 34b. When not being distinguished from each other, the tilting shafts 34a and 34b will be referred to as tilting shafts 34. When not being distinguished from each other, the bearings 35a and 35b will be referred to as bearings 35.

Further, the gantry 10 includes a cooling mechanism configured to discharge heat generated by the X-ray tube 23 during image taking processes to the exterior thereof. For example, the heat generated by the X-ray tube 23 is guided to the oil cooler 26 serving as a cooling mechanism by a circulation of insulating oil and is discharged from the interior of the rotating frame 22 in the direction toward the outer circumference. However, not all of the generated heat is discharged to the outer circumference. Some of the generated heat remains in the interior of the rotating frame 22. Further, the exhaust fans 27a and 27b are installed in a ceiling part of the cover 21. With this arrangement, the heat discharged to the interior of the rotating frame 22 is discharged to the exterior of the gantry 10 more efficiently through the exhaust fans 27a and 27b. When not being distinguished from each other, the exhaust fans 27a and 27b will be referred to as exhaust fans 27.

Figure 3A:
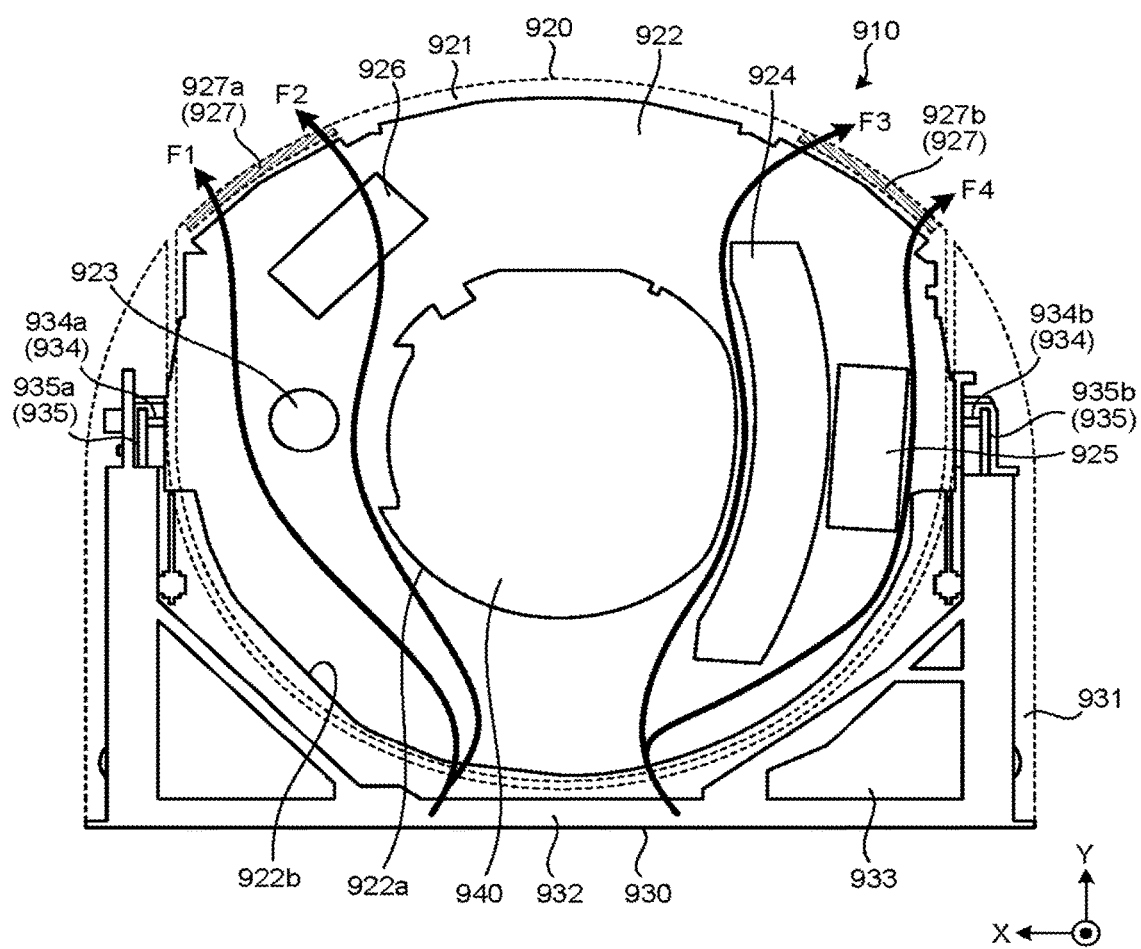
FIG. 3A is a drawing for explaining a cooling mechanism according to a conventional technique.
Figure 3B:
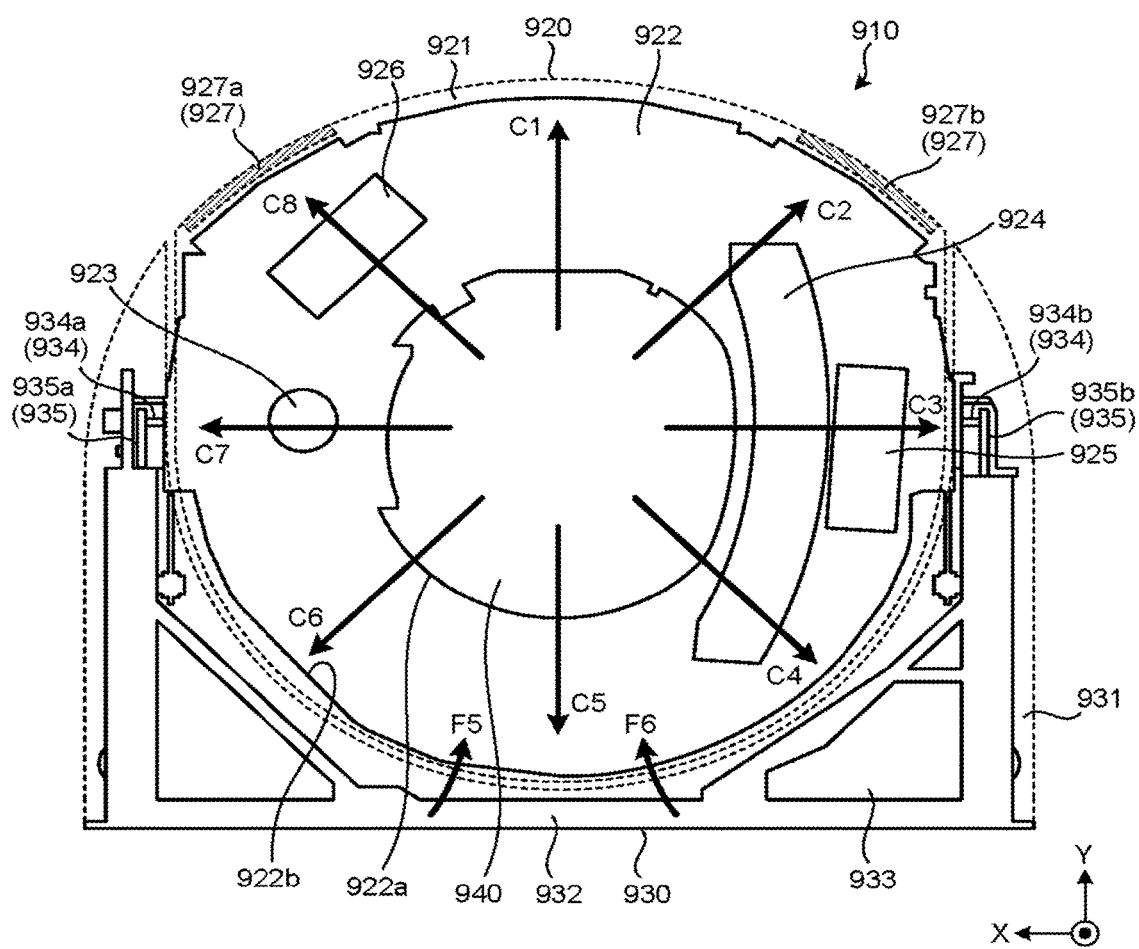
FIG. 3B is another drawing for explaining the cooling mechanism according to the conventional technique.

A cooling mechanism according to a conventional technique will be explained, with reference to FIGS. 3A and 3B. FIGS. 3A and 3B are drawings for explaining the cooling mechanism according to the conventional technique. FIGS. 3A and 3B illustrate a gantry 910 according to the conventional technique. The gantry 910 includes a rotating mechanism 920 and a fixing mechanism 930. The rotating mechanism 920 includes a cover 921 and a rotating frame 922. The rotating frame 922 includes, as constituent elements thereof, an X-ray tube 923, an X-ray detector 924, a DAS 925, and an oil cooler 926. Further, on the cover 921, exhaust fans 927a and 927b are installed.

As illustrated in FIG. 3A, the gantry 910 according to the conventional technique sucks the exterior air in from the floor face side of the gantry 910. In this situation, while the rotating frame 922 is stopped, the air sucked in from the floor face side of the gantry 910 is routed through the interior of the rotating frame 922 and is then discharged to the exterior of the gantry 910 through the exhaust fans 927a and 927b installed in a ceiling part of the cover 921. The air discharged through the exhaust fan 927a includes, as illustrated in FIG. 3A for example, a flow F1 routed through the outer circumferential side of the rotating frame 922 and a flow F2 routed through the inner circumferential side of the rotating frame 922. Further, the air discharged through the exhaust an 927b includes, as illustrated in FIG. 3A for example, a flow F3 routed through the outer circumferential side of the rotating frame 922 and a flow F4 routed through the inner circumferential side of the rotating frame 922. In this situation, the outer circumferential side of the rotating frame 922 denotes the vicinity of an annular region 922b of the rotating frame 922, whereas the inner circumferential side of the rotating frame 922 denotes the vicinity of an annular region 922a.

In contrast, in the gantry 910, while the rotating frame 922 is being rotated, it is difficult to suck in the exterior air from the floor face side of the gantry 910 to the interior of the rotating frame 922, due to centrifugal forces caused by the rotation of the rotating frame 922. More specifically, centrifugal forces C1 to C8 act on the rotating frame 922 being rotated, as illustrated in FIG. 3B, for example. As a result, exterior air flows F5 and F6 sucked in from the floor face side of the gantry 910 are pushed back to the floor face side by the centrifugal forces C4 to C6, for example, and it is therefore difficult for the exterior air flows F5 and F6 to be sucked into the interior of the rotating frame 922. As a result, in the rotating frame 922 being rotated, the formation of the air flows F1 to F4 illustrated in FIG. 3A is inhibited. For this reason, in order to cool the interior of the rotating frame 922 also while the rotating frame 922 is being rotated, it is necessary to directly send cool air to the inner circumferential side of the rotating frame 922.

For example, it may be possible to directly send cool air to the inner circumferential side of the rotating frame 922, by providing the gantry 910 with an air intake port in a position on the side of an opening 940. However, the gantry 910 has a possibility of being used during a surgical operation performed on a patient. During surgical operations, fluid such as blood or vomit of the patient may splatter near the opening 940 of the gantry 910. If the air intake port were provided on the opening 940 side, such fluid might adhere to the air intake port or might be sucked into the inside of air intake port. For this reason, it would not be desirable to provide the gantry 910 with the air intake port positioned on the opening 940 side.

Further, another technique is known by which an air intake port is provided on the floor face side in the front face of the gantry 910, so that the exterior air is sent to the inner circumferential surface of the rotating mechanism 920 through the air intake port via a duct. According to this technique, however, the air is proactively sucked in from the floor face side of the gantry 910 where dust and the like are easily accumulated, so that the air can be sent to the rotating mechanism 920. Because the rotating mechanism 920 includes sensitive component parts such as the X-ray detector 924, it is essential to remove unwanted substances by providing the air intake port with a filter, when this technique is implemented. However, such a filter may be clogged over the course of time, and the amount of intake air may decrease. In that situation, it will be impossible to cool the interior of the rotating frame 922. Further, because the air intake port is provided in the front face of the gantry 910, the noise is increased, and the burden on the patient is larger.

Figure 4:
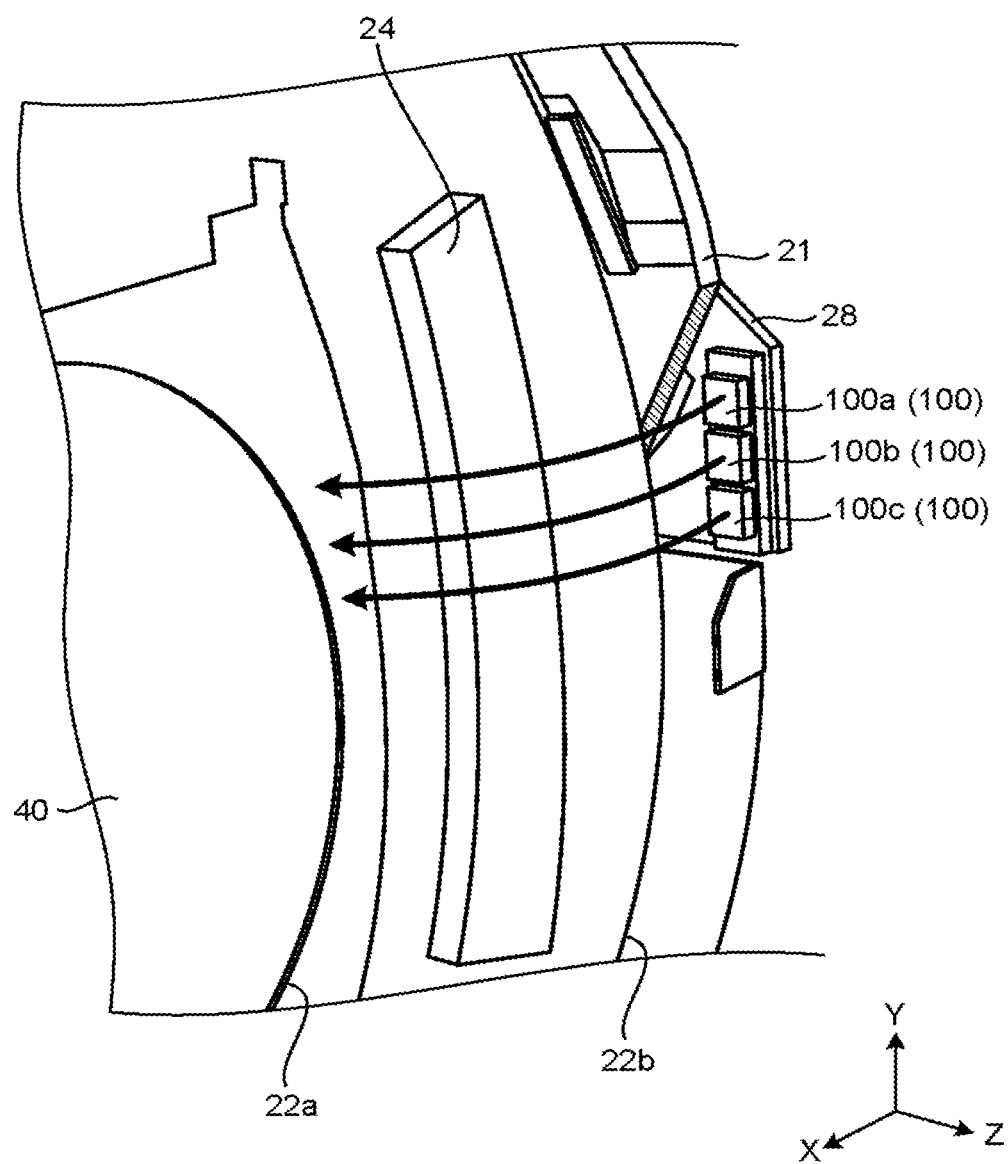
FIG. 4 is a drawing for explaining an air sending mechanism according to the first embodiment.
Figure 5A:
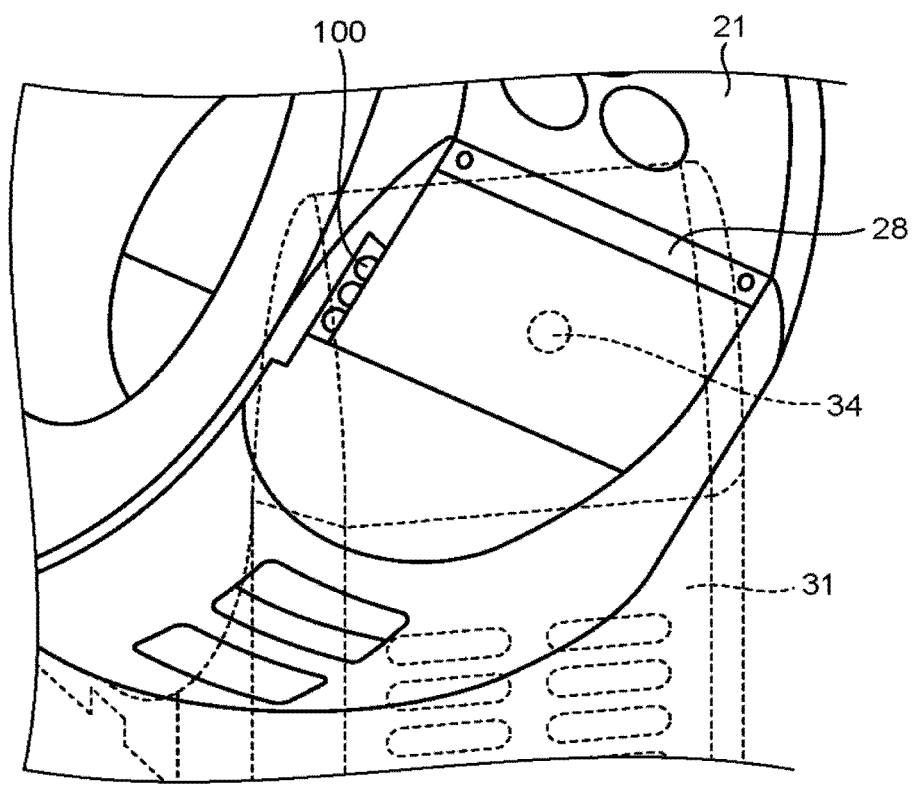
FIG. 5A is another drawing for explaining the air sending mechanism according to the first embodiment.
Figure 5B:
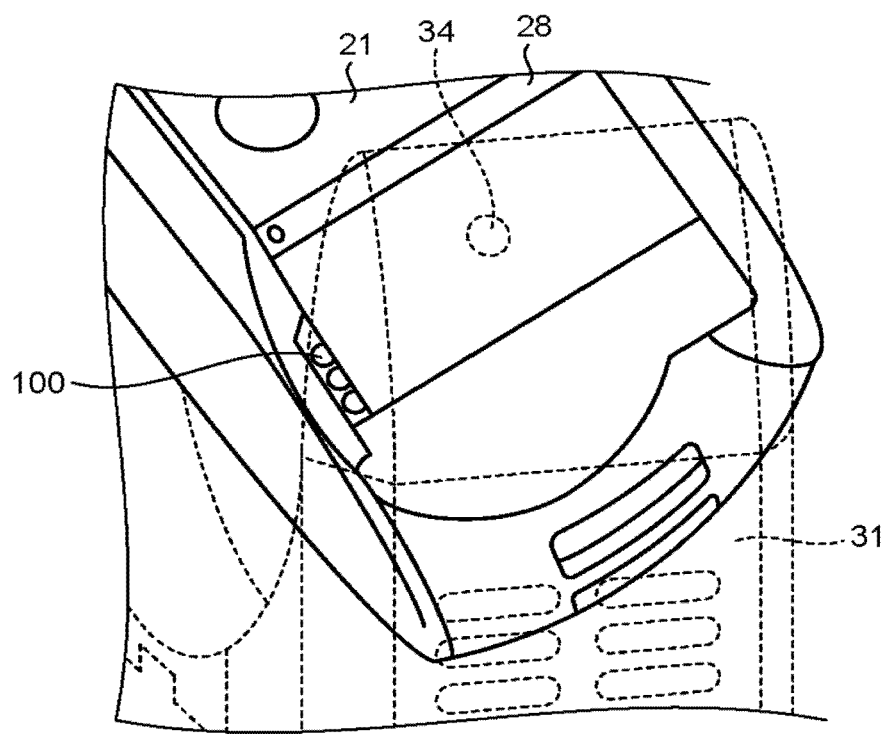
FIG. 5B is yet another drawing for explaining the air sending mechanism according to the first embodiment.

To cope with these situations, it is desirable to configure the gantry 10 so as to suppress noise and to cool the rotating frame 22 by sending air to the inner circumferential side of the rotating frame 22. Accordingly, in he first embodiment, an air sending mechanism is provided that is installed on a lateral face on the outer circumferential side of the rotating frame 22 with respect to the rotation axis and that is configured to send the air sucked in from the exterior of the rotating frame 22 to the rotation axis side of the rotating frame 22. The air sending mechanism according to the first embodiment will be explained, with reference to FIGS. 4, 5A, and 5B. FIGS. 4, 5A, and 5B are drawings for explaining the air sending mechanism according to the first embodiment. FIGS. 4, 5A, and 5B illustrate an example in which the air sending mechanism is an air intake fan.

FIG. 4 is a perspective view from the rotation axis side illustrating the right half of the rotating frame in FIGS. 1 and 2 that is positioned on the right side of the rotation axis. As illustrated in FIG. 4, a metal plate 28 is attached to the cover 21. Air intake fans 100a, 100b, and 100c are installed on the rotating frame 22 side of the metal plate 28. When not being distinguished from one another, the air intake fans 100a, 100b, and 100c will be referred to as air intake fans 100. The face of the metal plate 28 that is opposite of the face on which the air intake fans 100 are installed is configured to have a mesh-like structure, for example, so as to serve as an air intake port that allows the air intake fans 100 to suck in the exterior air.

In this situation, the air intake fans 100 are installed so as to be offset from the rotating frame 22. In the present example, being offset from the rotating frame 22 means that the air intake fans 100 are installed on the outside of the rotating frame 22 in terms of the rotation axis direction of the rotating frame 22. In other words, as being offset, the air intake fans 100 are installed on the outside of the rotating frame 22 on the cover 21, in terms of the rotation axis direction of the rotating frame 22. For example, as being offset, the air intake fans 100 are arranged in a position shifted, with respect to the rotating frame 22, at least one selected from between: to the front of the rotation plane on the front face side of the rotating frame 22 or to the rear of the rotation plane on the rear face side of the rotating frame 22 in terms of the rotation axis direction (the Z-axis direction in FIG. 4). In the example illustrated in FIG. 4, the air intake fans 100 are arranged, for instance, in a position to the front of the rotation plane on the front face side of the rotating frame 22 in terms of the rotation axis direction (the Z-axis direction in FIG. 4). Also, the air intake fans 100 are arranged so as to be tilted at a predetermined angle with respect to the rotation axis direction of the rotating frame 22. With these arrangements, as illustrated in FIG. 4, the air sucked in by the air intake fans 100 is caused to blow in a diagonal direction with respect to the rotation axis direction of the rotating frame 22. In other words, the air sucked in by the air intake fans 100 is sent to the inner circumferential side of the rotating frame 22. More specifically, as illustrated in FIG. 4, the air sucked in through the air intake fans 100 is, for example, sent to the region positioned between the X-ray detector 24 and the annular region 22a. As a result, even when being under the influence of the centrifugal forces while the rotating frame 22 is being rotated, the air intake fans 100 are able to send the sucked-in air to the interior of the rotating frame 22.

Further, the air sending mechanism is installed in the vicinity of at least one of the tilting shafts 34. FIG. 5A illustrates an example in which the rotating mechanism 20 is tilted at −30 degrees, whereas FIG. 5B illustrates an example in which the rotating mechanism 20 is tilted at +30 degrees. Further, in FIGS. 5A and 5B, the cover 31 and the tilting shaft 34 of the fixing mechanism 30 are indicated with broken lines. For example, as illustrated in FIGS. 5A and 5B, the air intake fans 100 are installed in the vicinity of the tilting shaft 34 on the cover 21 of the rotating mechanism 20.

With these arrangements, as illustrated in FIG. 5A for example, even when the rotating mechanism 20 is tilted at the angle of −30 degrees, no significant change occurs in the positional relationship between the air intake fans 100 and the cover 31 of the fixing mechanism 30. For this reason, it is possible to house the air intake fans 100 within the cover 31 of the fixing mechanism 30. Similarly, as illustrated in FIG. 5B for example, even when the rotating mechanism 20 is tilted at angle of +30 degrees, no significant change occurs the positional relationship between the air intake fans 100 and the cover 31 of the fixing mechanism 30. For these reasons, it is possible to house the air intake fans 100 within the cover 31 of the fixing mechanism 30.

As explained above, because the air intake fans 100 are installed in the vicinity of the tilting shaft 34, it is possible to house the air intake fans 100 on the inside of the cover 31 of the fixing mechanism 30 even when the rotating mechanism 20 is tilted. Further, the air intake fans 100 are installed on the lateral side of the gantry 10 positioned distant from the patient. As a result, it is possible to reduce the noise caused by the air intake fans 100.

As explained above, according to the first embodiment, the air intake fans 100 are configured to send the exterior air to the rotation axis side of the rotating mechanism 20 at all times regardless of whether the rotating frame 22 is being rotated or stopped. It is therefore possible to efficiently cool the interior of the rotating mechanism 20.

<A Modification Example of the First Embodiment>

Figure 6:
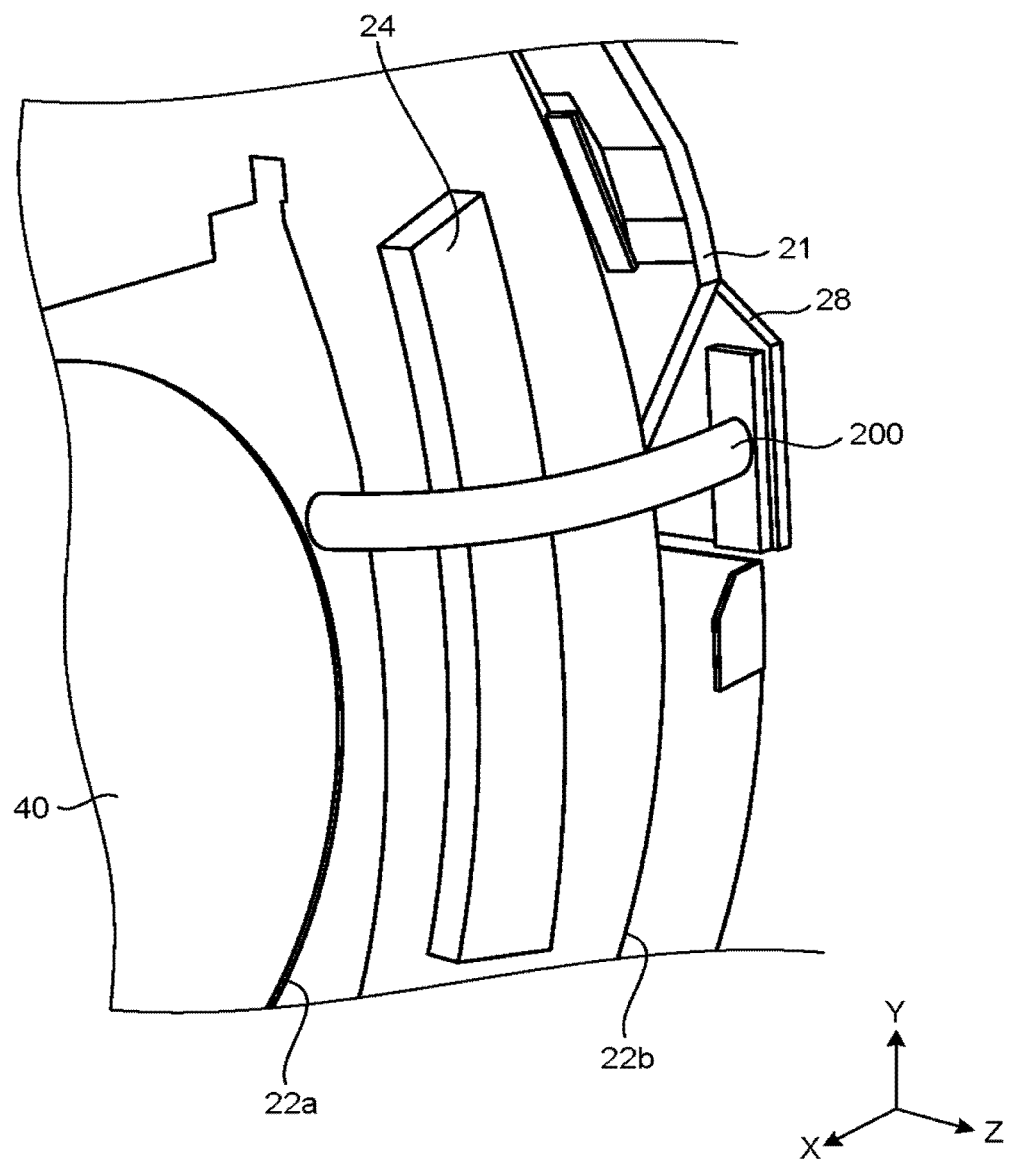
FIG. 6 is a drawing for explaining an air sending mechanism according to a modification example of the first embodiment.

In the first embodiment, the example in which the air sending mechanism is realized with the air intake fans 100 is explained; however, possible embodiments are not limited to this example. For instance, the air sending mechanism may be realized with a duct. FIG. 6 is a drawing for explaining an air sending mechanism according to a modification example of the first embodiment.

Similarly to FIG. 4, FIG. 6 is a perspective view from the rotation axis side illustrating the right half of the rotating frame 22 in FIGS. 1 and 2 that is positioned on the right side of the rotation axis. As illustrated in FIG. 6, the metal plate 28 is attached to the cover 21. A duct 200 is installed on the rotating frame 22 side of the metal plate 28. In this situation, the face of the metal plate 28 that is opposite of the face on which the duct 200 is installed is configured to have a mesh-like structure, for example, so as to serve as an air intake port that allows the duct 200 to suck in the exterior air. Similarly to the example in which the air intake fans 100 are installed as an air sending mechanism, the duct 200 is installed in the vicinity of the tilting shaft 34.

In this situation, as illustrated in FIG. 6, the duct 200 is a path extending from the cover 21 positioned on the outer circumferential side of the rotating frame 22 to the inner circumferential side of the rotating frame 22. In the example illustrated in FIG. 6, it is assumed that, for example, a driving mechanism such as a bearing is installed on the rear face side of the rotating frame 22, whereas the X-ray tube 23 and the X-ray detector 24 are installed on the front face side of the rotating frame 22. In that situation, the duct 200 is installed so as to be offset from the rotating frame 22. For example, in terms of the rotation axis direction, the duct 200 is arranged to be positioned at least one selected from between: on the front side or on the rear side of the rotating frame 22. More specifically, as illustrated in FIG. 6, the duct 200 is arranged on the front side of the rotation plane of the rotating frame 22 in terms of the rotation axis direction (the Z-axis direction in FIG. 6). Further, in the rotating frame 22, the duct 200 illustrated in FIG. 6 extends from the cover 21 on the outer circumferential side of the rotating frame 22 to a position on the inside of the opening 40 of the annular region 22a. In this situation, because the interior of the rotating frame 22 has negative pressure due to the rotation of the rotating frame 22, the exterior air is sucked in via the duct 200. Further, as illustrated in FIG. 6, the air sucked in by the duct 200 is directly sent the inner circumferential side of the rotating frame 22 without being influenced by the air flows within the rotating frame 22. More specifically, as illustrated in FIG. 6, the air sucked in through the duct 200 is sent to, for example, the region positioned between the X-ray detector 24 and the annular region 22a. Even when the rotating frame 22 is being stopped, because the interior of the rotating frame 22 has negative pressure due to the exhaust fans 27, the exterior air is sucked in via the duct 200. Accordingly, because the duct 200 is configured to send the exterior air to the rotation axis side of the rotating mechanism 20 at all times, regardless of whether the rotating frame 22 is being rotated or stopped, it is possible to efficiently cool the interior of the rotating mechanism 20.

In the embodiment above, the examples are explained in which the air sending mechanism is realized with either the air intake fans 100 or the duct 200; however, possible embodiments are not limited to these examples. For instance, the gantry 10 may include an air sending mechanism in which the air intake fans 100 and the duct 200 are combined together. In that situation, the duct 200 a configured to send the exterior air sucked in by the air intake fans 100 to the rotation axis side of the rotating frame 22. In this situation, when the air sending mechanism combining together the air intake fans 100 and the duct 200 is used, the air intake fans 100 and the duct 200 are installed so as to be offset from the rotating frame 22. For example, as being offset, the air intake fans 100 are installed on the outside of the rotating frame 22 in terms of the rotation axis direction of the rotating frame 22, similarly to the example in FIG. 4. Further, in that situation, the air intake fans 100 may be arranged so as to be tilted at a predetermined angle with respect to the rotation axis direction of the rotating frame 22. Alternatively, when being combined with the duct 200, the air intake fans 100 may be arranged, as being offset, so as to be tilted at a predetermined angle with respect to the rotation axis direction of the rotating frame 22, while being positioned on the inside of the rotating frame 22 in terms of the rotation axis direction of the rotating frame 22. For example, as being offset, the air intake fans 100 may be arranged on the cover 21 so as to be tilted at the predetermined angle with respect to the rotation axis direction of the rotating frame 22, while being positioned on the inside of the rotating frame 22 in terms of the rotation axis direction of the rotating frame 22. In other words, the air intake fans 100 are arranged so as to be offset from the rotating frame 22 by being tilted at the predetermined angle with respect to the rotation axis direction of the rotating frame 22, without the position thereof being shifted to the outside of the rotating frame 22 in terms of the rotation axis direction. When the gantry 10 includes the air sending mechanism in which the air intake fans 100 and the duct 200 are combined together, because the duct 200 is installed so as to be offset from the rotating frame 22, the air intake fans 100 do not necessarily have to be installed so as to be offset from the rotating frame 22, and the air intake fans 100 do not necessarily have to be arranged so as to be tilted at the predetermined angle with respect to the rotation axis direction of the rotating frame 22.

Further, in the embodiment described above, the example is explained in which the cover 21 has the air sending mechanism installed in the vicinity of the tilting shaft 34b; however, possible embodiments are not limited to this example. For instance, the air sending mechanism such as one or more of the air intake fans 100 and/or the duct 200 may be installed on the cover 21 in the vicinity of each of the tilting shafts 34a and 34b. For example, the gantry 10 may be configured so that the cover 21 has one or more of the air intake fans 100 installed in the vicinity of each of the tilting shafts 34a and 34b. Alternatively, the gantry 10 may be configured so that the cover 21 has the duct 200 installed in the vicinity of each of the tilting shafts 34a and 34b. In another example, the gantry 10 may be configured so as to include, as the air sending mechanism, one or more of the air intake fans 100 and the duct 200 independently of each other. For example, the gantry 10 may have one or more of the air intake fans 100 installed in the vicinity of the tilting haft 34a and may have the duct 200 installed in the vicinity of the tilting shaft 34b. In yet another example, the gantry 10 may have one or more of the air intake fans 100 installed in the vicinity of the tilting shaft 34a and may have an air sending mechanism combining together one or more of the air intake fans 100 and the duct 200 installed in the vicinity of the tilting shaft 34b. In yet another example, the gantry 10 may have the duct 200 installed in the vicinity of the tilting shaft 34a and may have an air sending mechanism combining together one or more of the air intake fans 100 and the duct 200 installed in the vicinity of the tilting shaft 34b.

Further, although the example in which the three air intake fans 100 are installed is explained with reference to FIG. 4, possible embodiments are not limited to this example. For instance, it is acceptable to arbitrarily change the number of air intake fans installed in the gantry 10.

Further, although the example in which the single duct 200 is installed is explained with reference to FIG. 6, possible embodiments are not limited to this example. For instance, it is acceptable to arbitrarily change the number of ducts 200 installed in the gantry 10. When two or more ducts are installed in the gantry 10, it is acceptable to install a duct 200a other than the duct 200 extending from the cover 21 on the outer circumferential side of the rotating frame 22 to the inner circumferential side of the rotating frame 22. For example, when two or more ducts are installed in the gantry 10, it is acceptable to further install, separately from the duct 200, the duct 200a extending from the front side of the rotation plane of the rotating frame 22 to the rear face side of the rotating frame 22, by being routed on the opening 40 side of the annular region 22a. In that situation, the duct 200a is able to send the air sent from the front side, also to the rear face side of the gantry 10.

With reference to FIG. 6, the example is explained in which the duct 200 is arranged on the front side of the rotation plane of the rotating frame 22 in terms of the rotation axis direction (the Z-axis direction in FIG. 6); however, possible embodiments are not limited to this example. For instance, when the driving mechanism such as the bearing is installed on the front face side of the rotating frame while the X-ray tube 23 and the X-ray detector 24 are installed on the rear face side of the rotating frame 22, the duct 200 may be arranged, for example, on the rear face side of the rotating frame 22 in terms of the rotation axis direction.

Further, the gantry 10 may be configured so as to cool primary heat sources by employing the air sending mechanism, even while the rotating frame 22 is stopped. For instance, the rotating frame 22 may be configured to stop in such a position that brings at least one selected from between the X-ray tube 23 and the X-ray detector 24, which are primary heat sources, into the proximity of the air sending mechanism. For example, when the air intake fans 100 are installed in the vicinity of the tilting shaft 34b, the rotating frame 22 may be stopped in such a position that brings the X-ray detector 24 in the proximity of the air intake fans 100, under the control of a console device.

Second Embodiment

In the first embodiment, the example is explained in which the air sending mechanism is provided so as to directly send the air sucked in from the exterior to the inner circumferential side of the rotating mechanism 20. In a second embodiment, an example will be explained in which air is sent to the inner circumferential side of the rotating mechanism 20, by providing a shaping mechanism configured to be able to shape the air flow formed by the rotation of the rotating frame 2 in the front-and-back direction with respect to the rotation axis. Because the overall configuration of the gantry 10 according to the second embodiment is the same as the exemplary configuration illustrated in FIGS. 1 and 2, the explanation thereof will be omitted.

Figure 7:
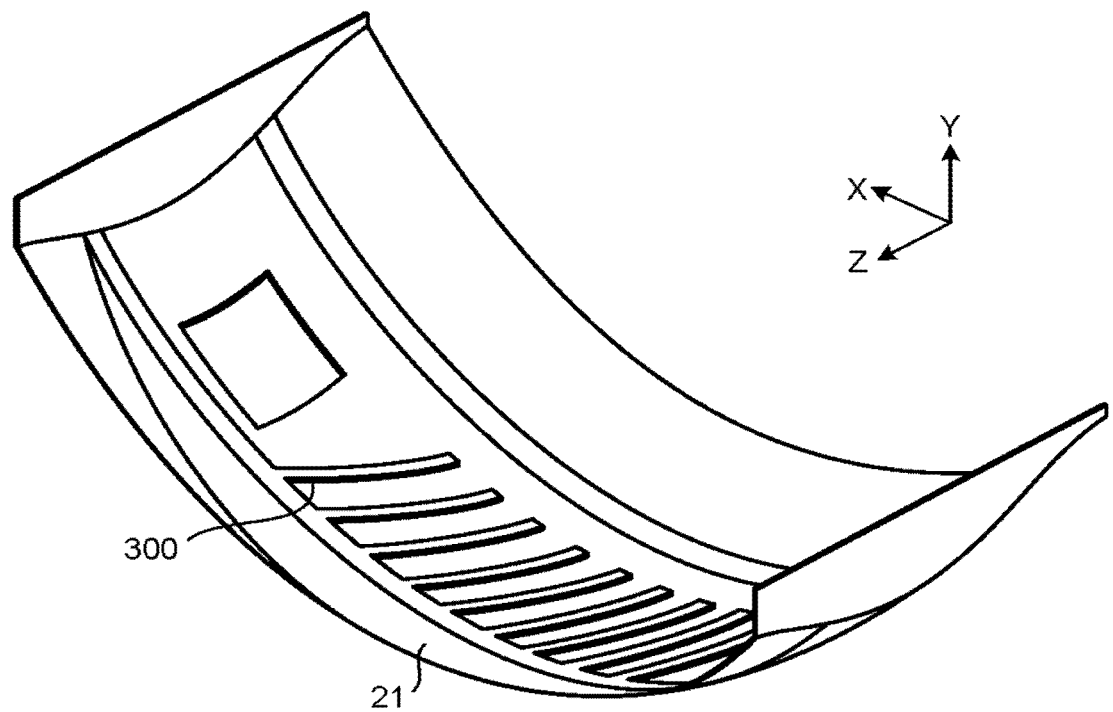
FIG. 7 is a drawing for explaining a shaping mechanism according to a second embodiment.
Figure 8:
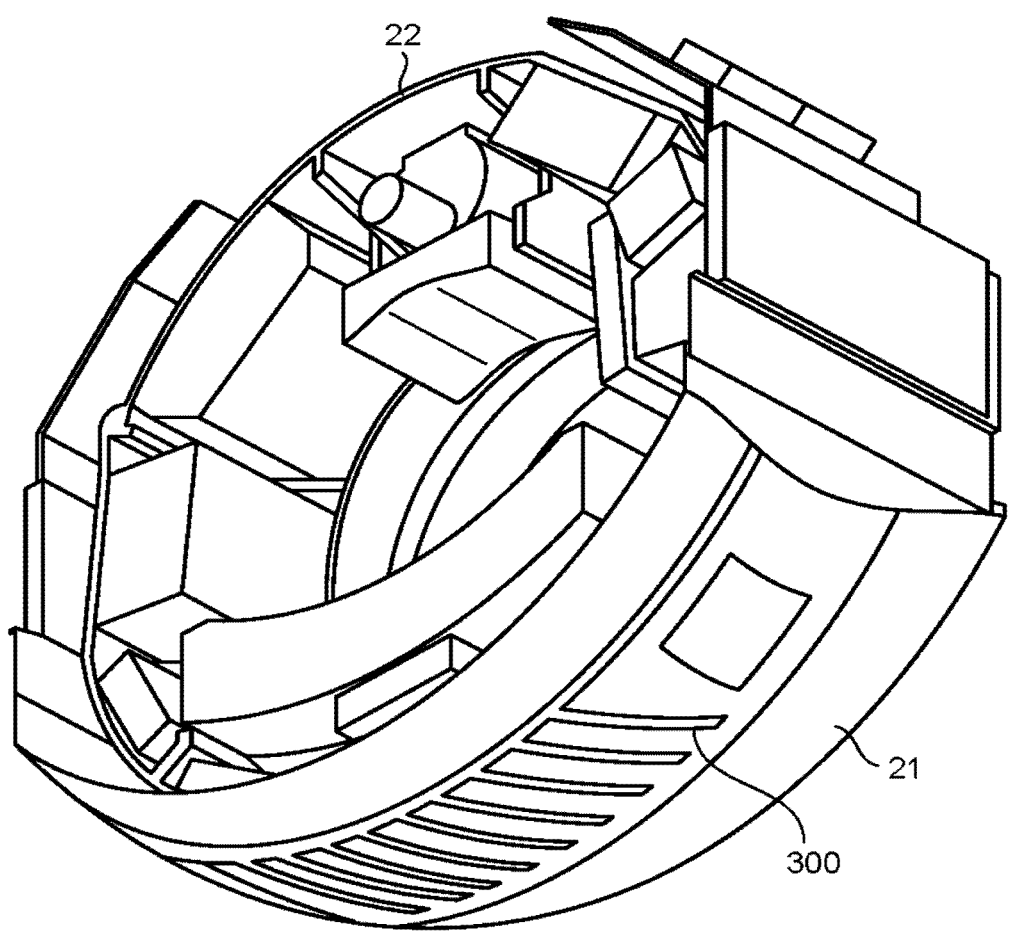
FIG. 8 is another drawing for explaining the shaping mechanism according to the second embodiment.
Figure 9:
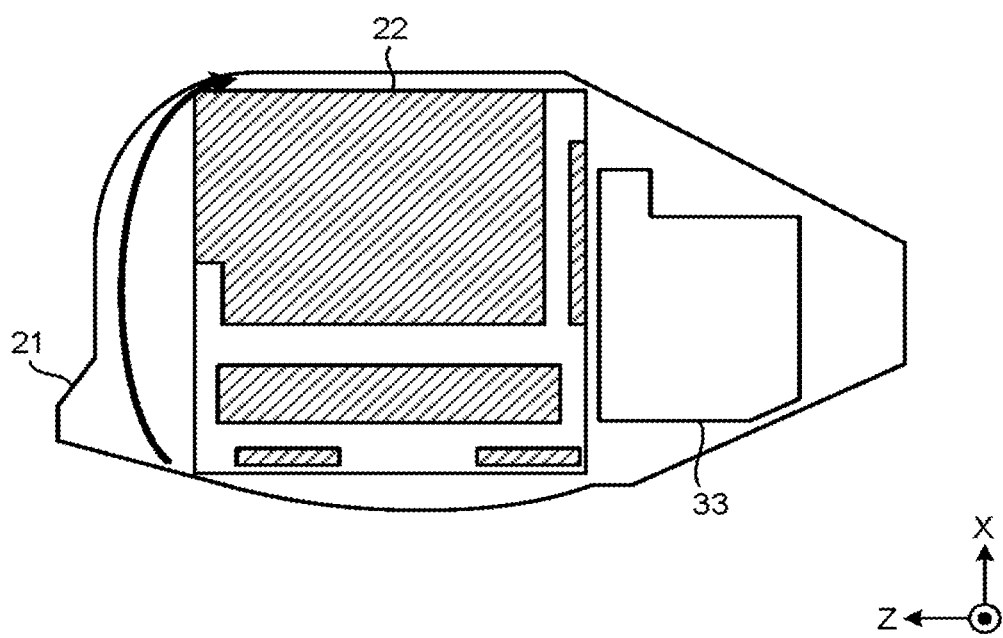
FIG. 9 is yet another drawing for explaining the shaping mechanism according to the second embodiment.

FIGS. 7 to 9 are drawings for explaining the shaping mechanism according to the second embodiment. With reference to FIGS. 7 to 9, an example will be explained in which fins 300 are formed on the cover 21 as the shaping mechanism, the fins 300 being configured to be able to shape the air flow formed by the rotation of the rotating frame 22 in the front-and-back direction with respect to the rotation axis.

FIG. 7 illustrates a bottom face part of the cover 21, whereas FIG. 8 illustrates the entirety of the cover 21 covering the rotating frame 22. FIG. 9 illustrates a cross-section of the gantry 10 illustrated in FIGS. 1 and 2, as the region in the right half positioned on the right side of the rotation axis of the gantry 10 is viewed from the Y-axis direction. In FIG. 9, the constituent elements includes in the rotating frame 22 are indicated with hatching. As illustrated in FIG. 7, the fins 300 are formed on the inner surface of the cover 21 of the rotating mechanism 20. In this situation, as illustrated in FIG. 8, the fins 300 are formed on at least the bottom face of the cover 21. As a result of the fins 300 being formed on the cover 21 in this manner, the direction of the flow of the air generated by the rotation of the rotating frame 22 is changed into a direction along the fins 300. In other words, the fins 300 are able to shape the air moving in the Z-axis direction of the gantry 10 as illustrated in FIG. 7, by using the rotation of the rotating frame 22. Further, as illustrated in FIG. 9, because the air shaped as illustrated in FIG. 7 flows along the cover 21, it means that the exterior air is eventually sent to the inner circumferential side of the rotating frame 22. In other words, because the fins 300 are forced on the cover 21, it is possible to supply the air generated within the rotating frame 22 to the rotation axis side of the rotating frame along the cover 21.

As explained above, according to the second embodiment, by forming the fins 330 on the inner surface of the cover 21 of the rotating mechanism 20, it is possible to change the direction of the air movement generated by the rotation of the rotating frame 22. As a result, without the need to suck air in from the exterior of the gantry 10, it is possible to send air to the inner circumferential side of the rotating frame 22 by utilizing the air movement generated within the rotating frame 22. Further, because the air movement generated within the rotating frame 22 is utilized, there is no impact from noise.

In the second embodiment, the example is explained in which the fins 300 are formed; however, possible embodiments are not limited to this example. For instance, it is acceptable to arbitrarily change the form of the shaping mechanism as long as it is possible to send air to the inner circumferential side of the rotating frame 22 similarly to the fins 300.

Other Embodiments

Possible embodiments are not limited to the embodiments described above.

For example, the gantry 10 according to the first embodiment may be configured to include the shaping mechanism explained in the second embodiment. In other words, the gantry 10 according to the first embodiment may further include the shaping mechanism configured to be able to shape the air flow formed by the rotation of the rotating frame 22, in the front-and-back direction with respect to the rotation axis. In that situation, the gantry 10 may include the air intake fans 100 as an air sending mechanism and may include the fins 300 as a shaping mechanism. Further, the gantry 10 may include the duct 200 as an air sending mechanism and may include the fins 300 as a shaping mechanism. In another example, the gantry 10 may include an air sending mechanism combining the air intake fans 100 and the duct 200 together as an air sending mechanism and may include the fins 300 as a shaping mechanism. In yet another example, the gantry 10 may include the air intake fans 100 and the duct 200 that are independent of each other as air sending mechanisms and may include the fins 300 as a shaping mechanism. In yet another example, the gantry 10 may include one selected from between the air intake fans 100 and the duct 200 as well as an air sending mechanism combining the air intake fans 100 and the duct 200 together as air sending mechanisms and may include the fins 300 as a shaping mechanism.

Further, in the embodiment above, the example is explained in which the air intake fans 100 are arranged, for instance, to the front of the rotation plane on the front face side of the rotating frame 22 in terms of the rotation axis direction (the Z-axis direction in FIG. 4); however, possible embodiments are not limited to this example. For instance, the air intake fans 100 may be arranged, for example, to the rear of the rotation plane on the rear face side of the rotating frame 22, in terms of the rotation axis direction (the Z-axis direction in FIG. 4).

Further, the gantry 10 according to any of the embodiments described above is controlled by a console device (not illustrated). For example, the console device is configured to reconstruct CT image data by using the projection data acquired by the gantry 10. Further, for example, the console device controls the rotating frame 22 so as to stop in such a position that brings at least one selected from between the X-ray tube 23 and the X-ray detector 24 into the proximity of the air sending mechanism. Further, for example, when the X-rays finish being emitted from the X-ray tube 23, the console device controls the rotating frame 22 so as to stop in such a position that brings the X-ray detector 24 into the vicinity of the tilting shaft and into the proximity of the air sending mechanism.

In the description of the embodiments above, the constituent elements of the apparatuses and devices illustrated in the drawings are based on functional concepts. Thus, it is not necessary to physically configure the constituent elements as indicated in the drawings. In other words, the specific modes of distribution and integration of the apparatuses and devices are not limited to the ones illustrated in the drawings. It is acceptable to functionally or physically distribute or integrate all or a part of the apparatuses and devices in any arbitrary units, depending on various loads and the status of use. For example, the positions in which the X-ray tube 23 and the X-ray detector 24 illustrated in FIG. 2 are arranged within the rotating frame 22 may be reversed in terms of the left and the right directions with respect to the rotation axis. In that situation, the DAS 25 is arranged in the vicinity of the X-ray detector 24, whereas the oil cooler 26 is arranged in the vicinity of the X-ray tube 23. Further, all or an arbitrary part of the processing functions performed by the apparatuses and devices may be realized by a CPU and a computer program that is analyzed and executed by the CPU or may be realized as hardware using wired logic.

The controlling method to stop the rotating frame 22 explained in the embodiments above may be realized by causing a computer such as a personal computer or a workstation to execute a control computer program (hereinafter, simply "control program") that is prepared in advance. The control program may be distributed via a network such as the Internet. Further, the control program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, and may be executed as being read by a computer from the recording medium.

According to at least one aspect of the embodiments described above, it is possible to efficiently cool the interior of the rotating mechanism.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gantry comprising:
   a rotating frame including an X-ray tube and an X-ray detector configured to detect X-rays emitted from the X-ray tube;
   a fixing mechanism configured to support the rotating frame so as to be rotatable on a rotation axis;
   a cover configured to cover the rotating frame; and
   an air sending mechanism that is installed on a lateral face on an outer circumferential side of the cover with respect to the rotation axis and is configured to send air sucked in from an exterior of the rotating frame to the rotation axis side of the rotating frame, wherein
   the air sending mechanism is installed so as to be offset from the rotating frame, to be tilted at a predetermined angle with respect to the rotation axis direction, and to be tilted with respect to a plane vertical to the rotation axis direction.

2. The gantry according to claim 1, wherein
   the fixing mechanism is capable of supporting the rotating frame so as to be tilted at a predetermined angle with respect to a tilting shaft, and
   the air sending mechanism is installed in a vicinity of the tilting shaft.

3. the gantry according to claim 1, wherein the air sending mechanism is an air intake fan.

4. The gantry according to claim 3, wherein
   the air sending mechanism further includes a duct, and
   the duct sends exterior air sucked in by the air intake fan to the rotation axis side of the rotating frame.

5. The gantry according to claim 3, wherein the air intake fan is, as being offset, installed on an outside of the rotating frame, in terms of the rotation axis direction of the rotating frame.

6. The gantry according to claim 4, wherein the air intake fan is, as being offset, installed on an outside of the rotating frame, in terms of the rotation axis direction of the rotating frame.

7. The gantry according to claim 4, wherein the air intake fan is, as being offset, installed so as to be tilted at a predetermined angle with respect to the rotation axis direction, while being positioned on an inside of the rotating frame in terms of the rotation axis direction of the rotating frame.

8. The gantry according to claim 1, wherein the air sending mechanism is a duct.

9. The gantry according to claim 1, further comprising: a shaping mechanism configured to be able to shape an air flow formed by a rotation of the rotating frame in a front-and-back direction with respect to the rotation axis.

10. The gantry according to claim 1, wherein the rotating frame is stopped in such a position that brings at least one selected from between the X-ray tube and the X-ray detector into proximity of the air sending mechanism.

11. The gantry according to claim 1, wherein, when the X-rays finish being emitted from the X-ray tube, the rotating frame is stopped in such a position that brings the X-ray detector into a vicinity of a tilting shaft and into proximity of the air sending mechanism.

12. A gantry comprising:
    a rotating frame including an X-ray tube and an X-ray detector configured to detect X-rays emitted from the X-ray tube;
    a fixing mechanism configured to support the rotating frame so as to be rotatable on a rotation axis;
    a cover configured to cover the rotating frame; and
    a shaping mechanism configured to be able to shape an air flow formed by a rotation of the rotating frame, in a front-and-back direction with respect to the rotation axis, wherein
    the cover has formed thereon a fin configured, as the shaping mechanism, to be able to shape the air flow formed by the rotation of the rotating frame, in the front-and-back direction with respect to the rotation axis.

13. The gantry according to claim 12, wherein the fin is formed on at least a bottom face of the cover.

* * * * *